(12) United States Patent
Wood

(10) Patent No.: US 6,406,699 B1
(45) Date of Patent: Jun. 18, 2002

(54) COMPOSITION AND METHOD OF CANCER ANTIGEN IMMUNOTHERAPY

(76) Inventor: Gary W. Wood, 6609 State Line Rd., Kansas City, MO (US) 64113

( * ) Notice: Subject to any disclaimer, the term of this patent is extended or adjusted under 35 U.S.C. 154(b) by 0 days.

(21) Appl. No.: 09/412,681

(22) Filed: Oct. 5, 1999

(51) Int. Cl.$^7$ .................. A61K 39/00; A61K 39/38; A61K 39/385; A61K 45/00; A61K 47/00
(52) U.S. Cl. ................ 424/184.1; 424/278.1; 424/193.1; 424/195.11; 424/198.1; 424/277.1
(58) Field of Search ............ 424/184.1, 193.1, 424/195.11, 198.1, 277.1, 278.1

(56) References Cited

U.S. PATENT DOCUMENTS

| | | |
|---|---|---|
| 5,126,132 A | 6/1992 | Rosenberg |
| 5,290,551 A | 3/1994 | Berd |
| 5,443,983 A | 8/1995 | Ochoa et al. |
| 5,484,596 A | 1/1996 | Hanna, Jr. et al. |
| 5,637,483 A | 6/1997 | Dranoff et al. |
| 5,679,356 A | 10/1997 | Bonnem et al. |
| 5,725,855 A | 3/1998 | Ochoa et al. |
| 5,728,388 A | 3/1998 | Terman |
| 5,766,920 A | 6/1998 | Babbitt et al. |

FOREIGN PATENT DOCUMENTS

| | | | |
|---|---|---|---|
| WO | WO 97/05239 | * | 2/1997 |

OTHER PUBLICATIONS

Kruse and Beck. Artificial–capillary–system development of human alloreactive cytotoxic T–lymphocytes that lyse brain tumours. Biotechnol. Appl. Biochem 25:197–205, 1997.*

David N. Liebowitz, M.D., Ph.D., and Carl H. June, M.D., "Recent Advances in Adoptive Immunotherapy," *American Society of Clinical Oncology*, 1092–9118/99:302–312 (1999).

Gregory E. Plautz, M.D. et al., "Systemic T Cell Adoptive Immunotherapy of Malignant Gliomas," *J. Neurosurg.*, vol. 89: 42–51 (1998).

Alfred E. Chang and Suyu Shu, "Current Status of Adoptive Immunotherapy of Cancer," *Crit. Rev. Oncol. Hem.*, 22:213–228 (1996).

Alfred E. Chang et al., "Adoptive Immunotherapy With Vaccine–Primed Lymph Node Cells Secondarily Activated With Anti–CD3 and Interleukin–2," *J. of Clin. Oncol.*, 15:796–807 (1997).

Jan B. Vermorken et al., "Active Specific Immunotherapy for State II and State III Human Colon Cancer: a Randomised Trial," *The Lancet*, 353:345–350 (1999).

Alfred E. Chang et al., "Clinical Observations on Adoptive Immunotherapy With Vaccine–Primed T–Lymphocytes Secondarily Sensitized to Tumor in Vitro," *Can. Res.*, 53:1043–1050 (1993).

Frank P. Holladay et al., "Autologous Tumor Cell Vaccination Combined With Adoptive Cellular Immunotherapy in Patients with Grade III/IV Astrocytoma," *J. Neuro.–Oncol.*, 27:179–189 (1996).

* cited by examiner

*Primary Examiner*—Sheela Huff
*Assistant Examiner*—Alana M. Harris
(74) *Attorney, Agent, or Firm*—Sonnenschein Nath & Rosenthal

(57) ABSTRACT

A cancer immunotherapy method and composition for treating cancer in a patient comprised of vaccinating a patient with a vaccine comprised of the patient's own malignancy and an immunologic adjuvant, removing primed peripheral blood T lymphocytes from the patient, stimulating the primed T lymphocytes to differentiate into effector lymphocytes in vitro, stimulating the effector T lymphocytes to proliferate in vitro, and infusing the effector T lymphocytes back into the patient.

12 Claims, 4 Drawing Sheets

Overall Survival

COMPOSITION AND METHOD OF CANCER ANTIGEN IMMUNOTHERAPY

BACKGROUND OF THE INVENTION

A. THE IMMUNE SYSTEM AND CANCER

The mammalian immune system uses two general adaptive mechanisms to protect the body against environmental pathogens. One is the non-specific (or innate) inflammatory response. The other is the specific or acquired (or adaptive) immune response. Innate responses are fundamentally the same for each injury. In contrast, acquired responses are custom tailored to the pathogen.

The immune system recognizes and responds to structural differences between self and non-self proteins. Proteins that the immune system recognizes as non-self are called "antigens". Pathogens express large numbers of highly complex antigens. Acquired immunity has specific "memory" for antigenic structures, and repeated exposure to the same antigen increases the response, which increases the level of induced protection against that particular pathogen.

Acquired immunity is mediated by specialized immune cells called B and T lymphocytes. B lymphocytes produce and mediate their functions through the actions of antibodies. B lymphocyte dependent immune responses are referred to as "humoral immunity" because antibodies are detected in body fluids. T lymphocyte dependent immune responses are referred to as "cell mediated immunity" because effector activities are mediated directly by the local actions of effector T lymphocytes. The local actions of effector T lymphocytes are amplified through synergistic interactions between T lymphocytes and secondary effector cells, such as activated macrophages. The result is that the pathogen is killed and thereby prevented from causing disease.

Cancer immunity is mediated exclusively by T lymphocytes, which means that it involves acquired cell mediated immunity and does not involve B lymphocytes or antibodies. An activated acquired immune response kills cancer cells and rejects the cancer.

Medical interventions often make use of the fact that acquired immune responses can be artificially manipulated. Exposing individuals to a weakened pathogen induces acquired immunity without causing disease and protects the individual against later exposure to the same pathogen. The general process of artificially inducing protective immune responses is called vaccination. Protective immunity to some pathogenic agents can be transferred from one individual to another using T lymphocytes. Although cancer immunity can be transferred between individuals using T lymphocytes, currently there are no accepted medical interventions that employ T lymphocyte transfer between individuals.

Vaccines are mainly useful for disease prevention. Vaccination has been used to induce protection against a wide variety of environmental pathogens, particularly viruses. The dramatic success that has been achieved with vaccines has led to a search for therapeutic applications. The search for a therapeutic AIDS vaccine is one well-known example. Unfortunately, manipulating the immune system to treat pre-existing disease has proven much more difficult than manipulating the immune system for protection. The only well-documented success against human disease has been achieved in rabies. Multiple vaccinations can prevent rabies from developing after exposure to the virus. The same general rationale has been applied to cancer treatment. The thought has been that, since, unlike viruses, cancers are relatively slow growing, it could be possible to use vaccines to slow or prevent further growth or spread. However, only very limited success has been achieved with cancer vaccines.

It is not intuitive that malignancies would be susceptible to immune manipulation. Malignant cells are genetically altered normal cells, not foreign pathogens. The immune system must be able to recognize malignant cells as non-self, and it must be possible to manipulate the immune system to reject cancer cells that may have spread to remote body sites. Although malignant cells are not actually foreign pathogens, there is widespread agreement that malignant cells can be recognized as non-self. Cancer antigens are generated from the genetic changes that cancer cells go through during malignant transformation and progression. See Srivastava, Do Human Cancers Express Shared Protective Antigens? Or the Necessity of Remembrance of Things Past, Semnin. Immunol. 8:295–302 (1996). However, the extent to which the immune system of patients with progressing cancers can be manipulated is extremely controversial. See Ellem et al., The Labyrinthine Ways of Cancer Immunotherapy—T Cell, Tumor Cell Encounter: "How Do I Lose The? Let Me Count The Ways," Adv. Canc. Res. 75:203–249 (1998). This is mainly due to the fact that, like attempts to use the immune system to treat infectious disease, attempts to manipulate the immune system for the therapeutic benefit of cancer patients have been largely unsuccessful. Controversy about the potential susceptibility of human cancer to immune manipulation also arises from the fact that it is widely believed that human malignancies are weakly immunogenic. Consequently, there have been very few systematic attempts to determine the relative immunogenicity of human cancers.

How do researchers determine whether a substance is antigenic or that an acquired immune response has been induced in an individual that has been exposed to an antigen? For humoral immunity, there is a myriad of in vitro assays for measuring an increase in serum antibody levels. It is infinitely more difficult, however, to determine that a cell mediated immune response has been induced. Over the years, in vivo protection assays have proven to be the most reliable indicators when the antigen is a pathogen. Protection assays work well when the antigen in question causes disease and when the studies are being performed in experimental models. An individual is vaccinated with the antigen in question, then challenged with increasing quantities of the pathogenic agent. Thus, in the case of cancer, mice are exposed to a cancer vaccine, then injected later with live cancer cells. If the cancer cells fail to grow, then the animal is immune and one can infer that an immune response was induced. That approach also can be used to quantitate and determine the specificity of the response.

Protection experiments cannot be used to measure anti-cancer immune responses in humans because it would be unethical to inject patients with cancer-causing cells. Since cancer antigens remain to be defined and cell mediated immune responses against cancer involve a complex, poorly understood interplay between several T lymphocyte subpopulations, there is no simple, reliable way to quantitate such responses in vitro. Instead, delayed type hypersensitivity ("DTW") skin testing assays were developed long ago as an alternative in vivo assay for cell mediated immunity. The DTH1 reaction takes advantage of the fact that an immune animal or human develops an acquired cellular immune reaction that is characterized by redness and swelling that occurs within 24 to 48 hours following injection of antigen into the site.

Although there are in vitro assays that may be able to be routinely used in the future, the DTH reaction is the only method that has been used so far to measure immune responses against a cancer antigens in humans. See Berd et al., Treatment of Metastic Melanoma with Autologous Tumor Cell Vaccine: Clinical and Immunologic Results in 64 Patients, J. Clin. Oncol. 8:1858–1865 (1990); Hoover & Hanna, Active Immunotherapy in Colorectal Cancer, Semin. Surg. Oncol. 5:436–440 (1989); Lehner et al., Postoperative Active Specific Immunization in Curatively Resected Colorectal Cancer Patients with a Virus-Modified Autologous Tumor Cell Vaccine, Cancer Immunol. Immunother. 32:173–178 (1990). The reasons for this are fourfold. First, although malignant cells are immunogenic, no specific human cancer antigen has yet been identified, characterized, and purified from such cells. Second, DTH responses, like tumor immunity, are mediated locally by a combination of activated Th1 lymphocytes and non-cytotoxic, Th1-like CD8 T lymphocytes. See Cher & Mosmann, Two Types of Murine Helper T Cell Clone. II Delayed-Type Hypersensitivity Is Mediated by TH1 Clones, J. Immunol. 138:3688–3694 (1987); Mody et al., CD8 Cells Play a Critical Role in Delayed Type Hypersensitivity to Intact Cryptococcus Neoformans, J. Immunol. 152:3970–3979 (1994). Third, tumor immunity has been shown to correlate with DTH responses to cancer antigens in animal models. See Puccetti et al., Use of a Skin Test Assay to Determine Tumor-Specific CD8+ T Cell Reactivity, Europ. J. Immunol. 24:1446–1452 (1994); Barth et al., Interferon γ and Tumor Necrosis Factor Have a Role in Tumor Regressions Mediated by Murine CD8+ Tumor-Infiltrating Lymphocytes, J. Exp. Med. 173:647–658 (1991). Finally, currently available in vitro assays for antigen specific T lymphocyte function in humans are technically difficult and unreliable.

B. CANCER IMMUNOTHERAPY: INNATE IMMUNE REsponse Strategies

Two general approaches have been used in attempts to stimulate the immune system to stop cancer progression. The first approach has been to stimulate innate immune responses. Generally, cancer patients are exposed to a biomodulator, such as Bacillus Calmette Guerin ("BCG"), interleukin-2 ("IL-2"), tumor necrosis factor ("TNF"), or interferon ("IFN"), in the hope that non-specifically activated immune cells will inhibit further cancer growth. Unfortunately, with few exceptions, these agents exhibit modest anti-cancer activity, and, like other chemotherapeutic agents, are highly toxic at effective concentrations.

A variation on this innate immunotherapy theme that also has been extensively evaluated has been to take advantage of the fact that biomodulators will increase the anti-cancer activity of immune cells (macrophages, natural killer ("NK") cells, and lymphocytes) in vitro. Exposing lymphocytes to high concentrations of agents such as IL-2 produces lymphokine activated killer ("LAK") cells, which are part of the innate immune system. Although LAK cells are better able to kill cancer cells than normal cells, they exhibit no specificity for cancer antigens. The rationale for therapeutic studies using LAK cells was that, if one could increase the killing capability of lymphocytes, those potentiated lymphocytes would be able to destroy progressing cancers in vivo.

Steven Rosenberg at the National Cancer Institute performed the first human trial of autologous LAK cells in 1985. LAK cells were generated from peripheral blood leukocytes ("PBL") from tumor patients. After culturing the cells in high concentrations of IL-2, the LAK cells were then injected back into the cancer patient. The patients also were exposed to high concentrations ($\geq 18$ MIU/patient/day) of IL-2 after they had received the LAK cells. See Rosenberg, U.S. Pat. No. 4,690,915. Significant tumor regressions were seen primarily in melanoma and renal cell cancer patients.

Subsequent studies using LAK cells focused on melanoma and renal cancers. In eight different studies, 190 melanoma patients yielded an overall response rate (complete and partial) of 16%. For renal cell cancer, 198 patients from eight different studies reported an overall response rate of 22%. See Chang, Current Status of Adoptive Immunotherapy of Cancer, Crit. Rev. Oncol. Hem. 22:213–228 (1996). However, it is generally believed that the therapeutic effects were due not to the adoptively transferred LAK cells but rather to the high concentrations ($\geq 18$ MIU/patient/day) of IL-2 that the patients received following infusion of the activated lymphocytes. Subsequent studies in animal models have been unable to document significant in vivo anti-tumor activity for LAK cells by themselves.

A variation on the same innate immunotherapy theme that was also championed by Stephen Rosenberg is the adoptive transfer of tumor infiltrating lymphocytes ("TIL"). TIL immunotherapy involves using high concentrations ($\geq 1000$ IU/ml) of IL-2 to stimulate mononuclear cells originally isolated from the inflammatory infiltrate present around solid tumors. The rationale is that TILs may be enriched for tumor specific cytolytic T lymphocytes and NK cells. Researchers theorized that the lymphoid infiltrate within a tumor represents a select population of immune cells which have preferentially migrated to the tumor. Unlike LAK cells, but like activated T lymphocytes, TIL cells are sometimes capable of lysing autologous cancer cells in a fashion that is highly specific and restricted by the major histocompatibility complex ("MHC") class I molecules. Researchers have claimed that TIL immunotherapy is 50–100 times more efficacious than LAK immunotherapy. a Rosenberg, U.S. Pat. No. 5,126,132; Rosenberg et al., Use of Tumor-Infiltrating Lymphocytes and Interleukin-2 in the Immunotherapy of Patients with Metastatic Melanoma, New Engl. J. Med. 319:1676–80 (1988). As with the LAK cell studies, it has been difficult to separate the in vivo effects of TIL from the anti-cancer effects of high dose IL-2.

Another variation on this general approach to generating non-specific effector cells for adoptive transfer to patients is to stimulate PBL from cancer patients with anti-CD3, a non-specific antigen receptor stimulus. See Ochoa et al., U.S. Pat. No. 5,443,983; Ochoa et al., U.S. Pat. No. 5,725, 855; Babbit et al., U.S. Pat. No. 5,766,920; Terman, U.S. Pat. No. 5,728,388. The idea was that patients should have circulating cancer antigen specific T lymphocyte precursors whose cancer fighting potential could be increased by stimulating them with anti-CD3 in culture. Such nonspecifically activated T lymphocytes also have no significant anti-tumor effects in vivo, despite the fact that they have been generated from the blood of cancer patients.

C. CANCER IMMUNOTHERAPY: ACQUIRED IMMUNE Response Strategies

The second general immunotherapeutic approach differs from the previous non-specific strategies mainly in that it is designed to induce, then augment, acquired immune responses against the patient's own cancer cells. The approach is predicated on the well-documented fact that the immune system normally fails to recognize and respond to progressing malignancies, but that it is possible to use vaccination to induce the cancer patient to respond immunologically to molecules expressed by malignant cells but not by normal cells. The basic rationale is that cancer could be successfully treated if one could induce a sufficiently powerful acquired immune response against cancer cell associated antigens.

The most successful strategies that have been tested in this category combine the fact that vaccination induces a protective immune response and that protective immunity can be transferred with activated T lymphocytes. The vaccination portion of this strategy often has been referred to as active specific immunotherapy ("ASI"). The term "active" is used because vaccination actively induces immune responses. The term "specific" is used because the strategy is designed to induce an immune response against antigens that are expressed by the patient's own cancer cells. The cell transfer portion of the strategy is generally known as adoptive cellular immunotherapy ("ACI"). The term "adoptive" is used because the strategy involves transferring immune effector cells from one site to another. The term "cellular" is used because the strategy involves transferring immune cells.

1. Active Specific Immunotherapy ("ASI")

The idea of ASI is well known in the art, and numerous ASI clinical trials have been performed using a wide variety of sources for cancer antigen. There are two basic reasons for taking this approach. Despite widespread controversy about the immunogenicity of particular human cancers, vaccines do induce cancer immunity. There is no theoretical reason why a powerful vaccine could not be therapeutic against cancer. If a vaccine can produce protective immunity that is sufficiently powerful to be therapeutic, it should be relatively simple to add it to the cancer treatment armamentarium.

Several general vaccine strategies are currently being explored. The simplest of those is to vaccinate patients with their own cancer cells. The whole cell approach has been tested for therapeutic efficacy in several human studies. One such study involved treating melanoma patients by vaccinating them with their own chemically altered cancer cells and BCG. See Berd, U.S. Pat. No. 5,290,551; Berd et al., Treatment of Metastatic Melanoma with Autologous Tumor Cell Vaccine: Clinical and Immunologic Results in 64 Patients, J. Clin. Oncol. 8:1858–1865 (1990). A second study involved treating colon cancer patients by vaccinating them with their own cancer cells and BCG. See Hanna, Jr. et al., U.S. Pat. No. 5,484,596; Vermorken et al., Active Specific Immunotherapy for Stage H and Stage III Human Colon Cancer: a Randomized Trial, Lancet 353:345–350 (1999).

Two general facts have become apparent about ASI. The first is that the source of cancer antigen is critical for success. At present, intact, viable cells from the patient's own cancer provide the best source. The second is that cancer antigen must be combined with an immunologic adjuvant to increase the potency of the vaccine. BCG has been used as the immunologic adjuvant for most human ASI clinical trials. BCG, however, has several disadvantages as an adjuvant, such as its relatively high toxicity and relatively low potency. More recent approaches to increasing the potency of autologous cancer cell vaccines have involved genetically altering the cancer cells to make them more immunogenic. One successful approach involved inserting the gene for the cytokine, granulocyte macrophage colony stimulating factor ("GM-CSF"), into tumor cells. See Bonnen et al., U.S. Pat. No. 5,679,356; Dranoff et al., U.S. Pat. No. 5,637,483; Dranoff et al., Vaccination with Irradiated Tumor Cells Engineered to Secrete Murine GM-CSF Stimulates Potent, Specific, Long-Lasting Anti-Tumor Immunity, PNAS (USA) 90:3539–3543 (1993). Very recent observations, however, suggest that simply mixing soluble GM-CSF with autologous cancer cells serves the same purpose. That is, GM-CSF, by itself is a very effective adjuvant.

In sum, the most potent currently available vaccine strategies will induce immune responses in most patients against their own cancer, and multiple vaccination may slow malignant progression. However, ASI by itself does not produce cures either in humans or in animal models.

2. Adoptive Cellular Immunotherapy ("ACI")

The idea of ACI also is well known in the art. The first documented experiments involving the cellular transfer of immunity occurred in 1942 when researchers found that DTH to simple chemical compounds could be transferred from sensitized (immune) donors to naïve (non-immune) recipients with cells from peritoneal exudates. See Landsteiner et al., Experiments on Transfer of Cutaneous Sensitivity to Simple Compounds, Proc. Soc. Exp. Biol. Med. 49:688–690 (1942). This is important for cancer therapy because vaccinating patients with their own cancer cells and an immunological adjuvant will induce strong DTH responses. See Hoover & Hanna, Active Immunotherapy in Colorectal Cancer, Semin. Surg. Oncol. 5:436–440 (1989); Lehner et al., Postoperative Active Specific Immunization in Curatively Resected Colorectal Cancer Patients with a Virus-Modified Autologous Tumor Cell Vaccine, Cancer Immunol. hImunother. 32:173–178 (1990). By 1954, the phrase "adoptive immunotherapy" had been coined to describe the acquisition of immunity in a normal subject as a result of transference of immunologically activated lymphoid cells. a Billingham et al., Quantitative Studies on Tissue Transplantation, Proc. R Soc. Exp. Biol. 143:58–80 (1954). The adoptive transfer of lymph node ("LN") cells in mice was reported a year later. a Michison, Studies on the Immunological Response to Foreign Tumor Transplants on the Mouse, J. Exp. Med. 102: 157–177 (1955).

Adoptive transfer of acquired immunity is extremely important because it is a technique that has allowed immunologists to dissect the cellular basis of the immune system. It is not intuitive that adoptive transfer of immune cells would provide a useful immunotherapeutic tool against disease. In fact, while adoptive transfer of immune T lymphocytes transfers protection in the same way that vaccination induces protection, the adoptively transferred lymphocytes by themselves provide little or no therapeutic benefit. They will not reject progressing cancers. Thus, while ACI is well known in the art, it is not obvious that ACI could provide the basis for a potent immunotherapeutic strategy against cancer.

3. Cancer Antigen Immunotherapy ("CAI")

The question researchers next asked was whether ASI and ACI, both of which are protective, could be combined in a way that produces an additive product that is both protective and therapeutic. The immunotherapeutic strategy, however, has to be able to reject preexistent disease. Humans already have cancer when attempts to manipulate the immune system are begun. In fact, even at diagnosis, they usually have more advanced disease than the experimental animals that are the targets for immunotherapy testing.

The rationale for combining ASI and ACI is that while neither vaccination nor adoptive transfer of activated leukocytes from cancer patients are sufficient to make cancers regress, perhaps the two could be synergistic. The immunologic basis for combining the two strategies is that it is essential to induce the patient's immune system to recognize and respond to antigens that are expressed by malignant cells. Vaccination accomplishes this. Once immune responses have been produced, T lymphocytes could be removed from the immune individual, their number and potency could be increased in the laboratory and they could be returned to the patient where they could travel to sites of cancer growth and reject the progressing cancers. Doing so would produce an overall increase in the number of effector T lymphocytes entering the tumor.

Proof of this principle was established in animal studies in which lymphocytes were removed from immune animals, stimulated with cancer cells and small amounts (≦100 IU/ml) of IL-2 in culture and adoptively transferred to tumor bearing animals. This combinatorial strategy was capable of permanently curing progressing cancer. See Cheever et al., Specific Adoptive Therapy of Murine Leukemia with Cells Secondarily Sensitized in vitro and Expanded in IL-2, Progr. Cancer Res. Ther. 22:127–133 (1982); Chou & Shu, Cellular Interactions and the Role of Interleukin 2 in the Expression and Induction of Immunity Against a Syngeneic Murine Sarcoma, J. Immunol. 139:2103–2109 (1987); Holladay et al., Cytotoxic T lymphocytes, but not Lymphokine Activated Killer Cells, Exhibit Anti-Tumor Activity Against Established Intracerebral Gliomas, J. Neurosurg. 77:757–762 (1992). Those studies clearly demonstrated that therapeutic failures associated with vaccination alone were related to the inability of vaccination to produce high numbers of cancer antigen specific effector T lymphocytes and that the deficiency could be addressed by further activating the T lymphocytes ex vivo in the laboratory and then adoptively transferring the activated cells to tumor bearers. Thus, combining ASI and ACI produced an effective therapeutic strategy.

Later studies demonstrated that immune cancer antigen-specific T lymphocytes could be stimulated to differentiate into effector T lymphocytes using non-specific antigen receptor stimuli such as anti-CD3. The critical step in these studies was that lymphocytes had to be primed with antigen prior to exposure to anti-CD3. See Yoshizawa et al., Specific Adoptive Immunotherapy Mediated by Tumor-Draining Lymph Node Cells Sequentially Activated with Anti-CD3 and IL-2, J. Immunol. 147:729–737 (1991); Saxton et al., Adoptive Transfer of Anti-CD3 Activated CD4+ T Cells Plus Cyclophosphamide and Liposome Encapsulated Interleukin 2 Cure Murine MC-38 and 3LL Tumors and Establish Tumor Specific Immunity, Blood 89:2529–2536 (1997); Shu et al., Stimulation of Tumor-Draining Lymph Node Cells with Superantigenic Staphylococcal Toxins Leads to the Generation of Tumor-Specific Effector T cells, J. Immunol. 152: 1277–88 (1994); Baldwin et al., Ex Vivo Expansion of Tumor Draining Lymph Node Cells Using Compounds which Activate Intracellular Signal Transduction, J. Neuro. Oncol. 32:19–28 (1997). A wide variety of experimental cancers have been shown to be susceptible to these strategies.

The combination of cancer antigen vaccination and adoptive transfer of activated T lymphocytes is known as cancer antigen immunotherapy ("CAI"). This combinatorial strategy should be distinguished from other forms of ASI and ACI, particularly those that do not directly involve inducing an acquired immune response against the patient's own cancer cells.

Chang and his colleagues were the first to report the application of a form of CAI to humans. They vaccinated melanoma and renal cell cancer patients with irradiated autologous cancer cells and BCG. Lymphocytes then were obtained from LNs draining vaccination sites and stinulated in vitro with autologous cancer cells and low-dose IL-2 and infused into patients with concomitant intravenous admnin-istration of low-dose IL-2. See Chang et al., Clinical Observations on Adoptive Immunotherapy With Vaccine-Primed Lymphocytes Secondarily Sensitized with Tumor In Vitro, Canc. Res. 53:1043–1050 (1993). No clinically significant results were observed.

Holladay and his colleagues performed a similar study in patients with advanced brain cancer. Patients were vaccinated with their own cancer cells and BCG. Peripheral blood T lymphocytes were stimulated with autologous tumor cells and low-dose IL-2 in vitro and reinfused to the patients. S Holladay et al., Autologous Tumor Cell Vaccination Combined With Adoptive Cellular Immunotherapy in Patients with Grade III/IV Astrocytoma, J. Neuro-Oncol. 27:179–189 (1996). Again, no clinically significant results were observed.

More recently, Chang's group substituted anti-CD3 for tumor cells as the in vitro T lymphocyte stimulus. Se Chang et al., Adoptive Immunotherapy with Vaccine Primed Lymph Node Cells Secondarily Activated with Anti-CD3 and Interleukin-2, J. Clin. Oncol. 15:79–807 (1997). Lymphocytes then were obtained from LNs draining vaccination sites and stimulated in vitro with anti-CD3 and low-dose IL-2 and infused into patients with concomitant intravenous administration of IL-2. Some of the treated cancers regressed, but survival of the patients was not significantly prolonged.

Another group of researchers studied the feasibility, toxicity, and potential therapeutic benefits of another form of CAI in patients with malignant brain tumors. See Plautz et al., Systematic T Cell Adoptive Immunotherapy of Malignant Gliomas, J. Neurosurg. 89:42–51 (1998). Lymphocytes were obtained from LNs draining vaccination sites and stimulated in vitro with staphylococcal enterotoxin A, anti-CD3 and IL-2 and infused into patients with concomitant intravenous administration of IL-2. Again, no clinically significant results were obtained.

From the considerable variety of immunological cancer treatment strategies, it should be clear that there is no intuitively obvious CAI strategy. Nor is there any strategy that has established itself as the best immunologic treatment for human cancer. There is no FDA-approved immunotherapeutic approach to cancer treatment. Even among imnmunotherapists, there is a widespread belief that only a few melanomas and renal cell cancers express some modest immunogenicity and that human malignancies other than melanoma and renal cancer are non-immunogenic and therefore not susceptible to immunotherapy. Accordingly, few of the clinical studies involving immunotherapy have involved the treatment of human cancers other than melanoma or renal cancer, which are relatively uncommon cancers. There also is a widespread belief that, even if human cancers are immunogenic, antigen-specific tolerance and immune suppression would prevent generation of productive immune responses. See Ellem et al., The Labyrinthine Ways of Cancer Immunotherapy—T Cell, Tumor Cell Encounter: "How Do I Lose The? Let Me Count the Ways," Adv. Canc. Res. 75:203–249 (1998).

The considerable success that has been achieved using CAI in preclinical models predicts that CAI should be at least moderately successful as a treatment for human cancer. Yet, the clinical findings that have been obtained to date in human phase I/II clinical trials do not support such a claim. While the disparity could be attributable to fundamental immunological differences between human and experimental malignancies or the fact that it is not technically possible to implement CAI in humans, this is probably not the explanation. The disparity is most likely not due to conceptual or technical shortcomings in translating CAI from animals to humans, but rather to inappropriate expectations. There was no substantive difference in vaccination strategies nor in the effects of vaccination in experimental animals and humans. Humans and experimental animals both have been successfully vaccinated with whole cancer cells and an immunological adjuvant to induce an immune response against their own malignant cells. Autologous cancer antigen-specific T lymphocytes have been successfully obtained from lymphoid tissue and those T lymphocytes have been successfully activated in vitro in experimental animals and humans. In both cases, those T lymphocytes have exhibited the ability to destroy tumor in vitro. It has been possible to infuse activated T lymphocytes into the bloodstream of experimental animal and human cancer-bearing individuals. The infused T lymphocytes exhibited the ability to produce regression of growing cancers in both experimental animals and humans. Yet, the difference in results has been dramatic. 100% of treated animals were cured in most model systems, while significant anti-cancer effects were observed in only a small proportion of treated cancer patients, and few cures have been documented.

Based on the foregoing, there clearly exists a need to develop a CAI strategy that is effective, non-toxic, and feasible in human cancer patients.

SUMMARY OF THE INVENTION

The present invention relates to a cancer antigen immunotherapy strategy for use in treating various types of cancer in humans. More specifically, the present invention is directed to a method of treating cancer comprising the steps of vaccinating a patient with a vaccine comprised of a patient's own malignancy and an immunologic adjuvant, removing cancer antigen primed PBL from the patient, stimulating primed T lymphocytes to differentiate into effector lymphocytes in vitro, stimulating effector T lymphocytes to proliferate in vitro, and infusing the effector T lymphocytes back into the patient.

DESCRIPTION OF THE INVENTION

A. CANCER ANTIGEN IMMUNOTHERAPY

Step 1: Vaccination

Figure 1:
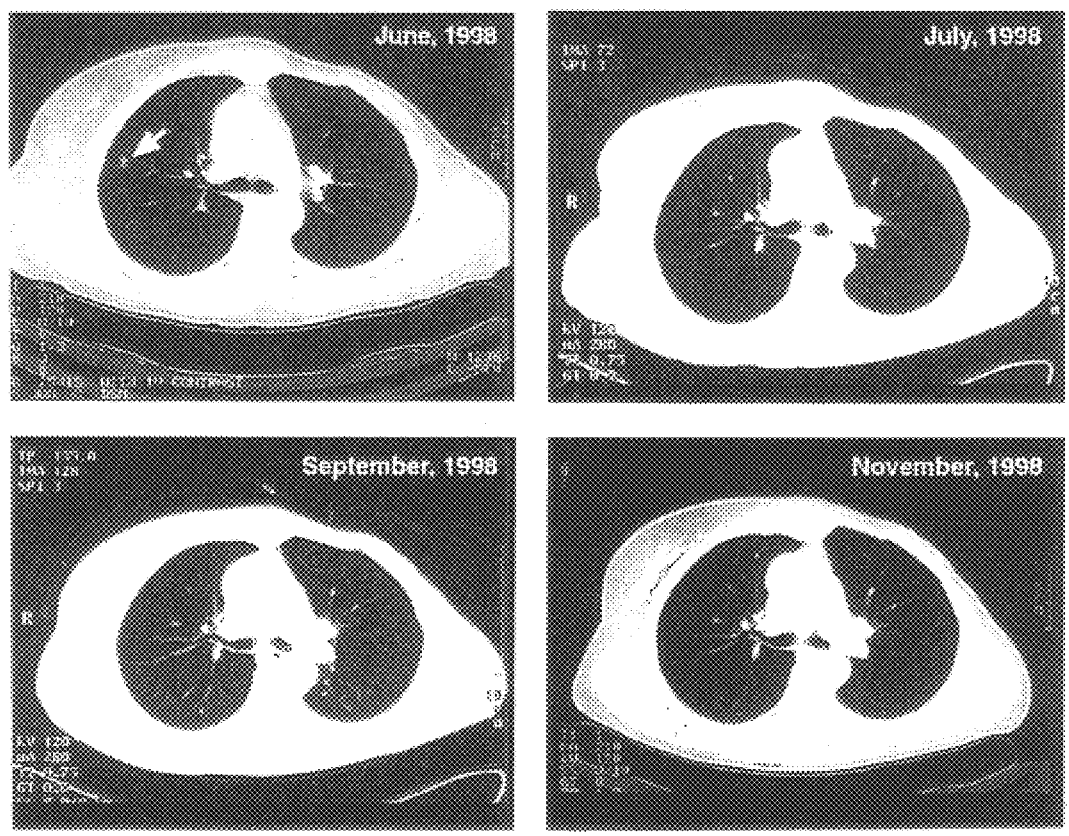
FIG. 1 shows serial cat scans of patient HT-98-3 which depict cancer regression following CAI. The patient received high dose chemotherapy in March 1998. CAI was delivered on Jun. 29, 1998 and Aug. 25, 1998. The arrow identifies a parenchymal mass.

The first step in the present invention is the immunization of patients with antigens from their own malignancy. In patients who have a solid malignancy, the cancer is surgically removed to create a single cell suspension of malignant cells. The surgical specimen is enzymatically digested with enzymes manufactured by Life Technologies, Inc. under the name VIACELL. In patients who have hematologic malignancies or solid malignancies with free cells in pleural, pericardial or peritoneal fluid, the malignant cells are obtained from the blood, bone marrow, pleural or pericardial effusion, or ascites fluid. The isolated malignant cells are irradiated at about 5,000 rads to prevent local growth. The cells are stored frozen until the vaccination is performed.

At the time of vaccination, the malignant cells are combined with an immunologic adjuvant, preferably soluble recombinant human GM-CSF that is manufactured by Immunex, Inc. under the name Leukine®. In the preferred embodiment, the vaccine is administered intradermally, subcutaneously, or intramuscularly to multiple (approximately 3 to 4) body sites. Each injection site receives at least 5×106 malignant cells and at least 100 micrograms of GM-CSF. Since the irradiated malignant cells are non-toxic, higher numbers could be safely injected to improve the immune response.

Patients are then injected with about 100 micrograms/site of GM-CSF daily for at least three days at the original vaccination sites. Other concentrations or other vaccination formulations of GM-CSF may also be effective. Since the irradiated malignant cells are nontoxic, multiple vaccinations can be safely performed to improve the immune response.

In a separate embodiment, the vaccine is comprised of an antigen expressed by the patient's own malignancy such that primary activation of the patient's T lymphocytes is induced. For example, the antigen may be a purified extract of the cancer or a genetically engineered antigen or antigenic peptide that is shared between cancers.

Step 2: Production and Proliferation of Effector T Lymphocytes

The second step in CAI involves the activation of peripheral blood T lymphocytes from the immunized patients. Local immunization leads to production of primed antigen-specific T lymphocytes in lymphoid tissue draining the immunization sites. The primed T lymphocytes are then released from lymphoid tissue into the blood so that they may be carried to the sites of the antigen exposure. Since primed T lymphocytes are released into the blood, peripheral blood should provide the richest source of cancer antigen specific T lymphocyte effector precursors. The preferred method for obtaining the peripheral blood lymphocytes is by leukapheresis. The preferred time for performing leukapheresis is within two weeks following the second vaccination.

In the preferred embodiment, the activation and proliferation of T lymphocytes occurs during in vitro cell culture as the result of a cooperative interaction between adherent monocytes and non-adherent T lymphocytes. Red blood cells ("RBCs") are removed from the leukapheresis sample by selective lysis with Tris-ammonium chloride. Peripheral blood mononuclear cells are then cultured in plastic tissue culture flasks that allow cell attachment in tissue culture medium containing serum. Autologous serum is used, but other serum sources may be substituted.

In the preferred embodiment, the peripheral blood T lymphocytes are stimulated in culture with mouse monoclonal anti-CD3 that is manufactured by Ortho Pharmaceuticals under the name OKT3™. However, other non-specific T-lymphocyte stimuli, such as staphylococcus enterotoxin or bryostatin-1 may be substituted for the anti-CD3. While the stimulus need not be able to bind to the antigen receptor or to antigen receptor associated proteins, the stimulus must be capable of stimulating primed T cells to differentiate into effector T lymphocytes that maintain tumor antigen specificity and effector activity. In the preferred embodiment, the optimal concentration of anti-CD3 for stimulating differentiation of antigen primed T lymphocytes into effector T lymphocytes is between 0.01 and 100.0 nanograms/milliliter. In the preferred embodiment, peripheral blood T lymphocytes are exposed to anti-CD3 for about 24 to 48 hours, then IL-2 is added to the cultures. Interleukin-2 is manufactured by Chiron Pharmaceutical, Inc. under the name Proleukin®.

In the preferred embodiment, the stimulated effector cells are proliferated in culture using IL-2. Other cytokines capable of stimulating proliferation of T lymphocytes, such as IL-15, may be substituted for IL-2. In the preferred embodiment, the optimal concentration of IL-2 for stimulating proliferation of activated T lymphocytes is between about 10 and 100 IU/milliliter.

Step 3: Infusion of Activated T Lymphocyles

After the stimulated cells have been harvested from culture, the cells are infused intravenously. Although the patient generally is infused with about $10^{10}$ to $10^{12}$ lymphocytes during a period of about 1 to 6 hours, the number of mononuclear cells administered is solely dependent upon the number of cells generated during the proliferation step. Over $10^{12}$ autologous lymphocytes have been safely infused into cancer patients.

The present invention will be further explained more specifically by the following examples. However, the scope of the present invention is not limited to the examples.

B. Breast Cancer Example

Step 1: Vaccination

In this example, all eligible patients had operable, histopathologically confirmed stage IV carcinoma of the breast and had failed standard chemotherapy for stage IV (metastatic) breast cancer.

Fresh tumor specimens were obtained sterilely at the time of surgical resection. As shown in Table 1, specimens were obtained from various body sites. Specimens were transported to the laboratory in isotonic saline at ambient temperature. The tissue was processed sterilely. Single cell suspensions were prepared by stirring tissue fragments for about 2 to 3 hours at approximately 37° C. in an enzyme mixture in a trypsinization flask. Cells were counted and viability was determined by trypan blue exclusion. A portion of the cells was cultured in tissue culture medium supplemented with about 20% fetal bovine serum to develop cell lines from patients' malignant cells and to test sterility. The remainder of the cells were irradiated at approximately 5,000 rads and stored frozen at about −70° C. in tissue culture medium supplemented with antibiotics, about 10% dimethylsulfoxide and about 20% human serum.

Immediately prior to vaccinating patients, frozen cells were thawed and suspended in tissue culture medium supplemented with about 20% human AB+ serum. Approximately $10^7$ cells from the original cancer specimen were sedimented, then mixed with 1.0 ml of GM-CSF (500 micrograms).

TABLE 1

Tumor characteristics

| Patient # | Site | # Tumor cells[1] | % Viability | Sterility[2] | Cell line[3] |
|---|---|---|---|---|---|
| HT-95-23 | Abdominal wall | $2 \times 10^7$ | 90 | + | + |
| HT-95-50 | Ascites | $3 \times 10^8$ | 99 | + | + |
| HT-95-57 | Lymph node | $3.2 \times 10^6$ | 80 | + | + |
| HT-95-12 | Lung | $1.5 \times 10^8$ | 75 | + | + |
| HT-95-56 | Breast | $<10^6$ | 85 | + | + |
| HT-96-62 | Breast | $2.7 \times 10^7$ | 93 | + | + |
| HT-96-4 | Breast | $7.1 \times 10^7$ | 89 | + | + |
| HT-96-32 | Breast | $6.2 \times 10^6$ | 95 | + | + |
| HT-96-47 | Lung | $4.0 \times 10^8$ | 70 | + | + |
| HT-97-3 | Lung | $1.0 \times 10^8$ | 99 | + | + |
| HT-97-4 | Chest wall | $4.0 \times 10^7$ | 99 | + | + |
| HT-97-6 | Lymph node | $4.3 \times 10^7$ | 93 | + | + |
| HT-98-1 | Lung | $6.8 \times 10^7$ | 94 | + | + |
| HT-98-3 | Chest wall | $3.0 \times 10^7$ | 95 | + | + |
| HT-98-15 | Lung | $6.1 \times 10^8$ | 95 | + | − |
| HT-98-18 | Chest wall | $7.3 \times 10^7$ | 90 | + | + |
| HT-98-73 | Liver | $2 \times 10^7$ | 75 | + | + |
| HT-99-2 | Breast | $3 \times 10^7$ | 80 | + | + |
| HT-99-35 | Lymph node | $1 \times 10^7$ | 95 | + | + |

[1] Number of cells obtained from surgical specimen. Additional cells were obtained for vaccination and skin testing by growing cells in culture.
[2] (+) - No microbial growth.
[3] (+) - Tumor cells grew out from surgical specimen.

The tumor cells were injected into three or four intradermal sites, bilaterally in the anterior upper thigh and bilaterally in the anterior upper chest. Patients who had had total mastectomies with unilateral removal of draining LNs were injected only into three sites. The injection volume was approximately 0.25 ml/site. The initial injection sites were marked, and each site was reinjected with about 100 micrograms of GM-CSF daily for an additional 4 days. A second vaccination containing $10^7$ tumor cells and a similar amount of GM-CSF was identically delivered to the same general area two weeks later.

Patients were skin-tested to assess the development of an autologous cancer antigen specific DTH response at the time of the second vaccination. The theory underlying DTH skin testing is that a DTH reaction occurs because some primed cancer antigen-specific T lymphocytes leave the peripheral blood, enter the skin, and interact with the cancer antigen and antigen presenting cells to produce a local immune response. The intensity of the response is directly proportional to the diameter of the erythema and induration that occurs locally at the injection site and the number of antigen-specific T lymphocytes that enter the site. In other words, the intensity of the response is directly proportional to the immunity that the individual possesses to the antigen that was used for skin testing. Therefore, skin testing provides a simple and reliable in vivo assay for cancer immunity that requires relatively small numbers of cancer cells. The DTH response provides a well-established measure of cell mediated immunity that has been extensively studied in experimental animals and humans. Response intensity has been shown to correlate directly with protective immunity in countless natural and experimental model systems. Response intensity has also been shown to correlate directly with results of various in vitro immune function assays.

Skin testing was performed by injecting about $10^7$ cancer cells intradermally on the left anterior forearm. When available, cultured cancer cells were used for skin testing. Cultured cancer cells were free of digestion enzyme and human serum proteins because the cells had been grown through several passages in medium containing fetal bovine serum. Also, multiple passages in culture are believed to eliminate contaminating stromal cells that do not replicate as rapidly as the malignant cells. Reactions against GM-CSF or contaminants associated with the GM-CSF were excluded because GM-CSF also was not included with the skin-test reagent. Thus, autologous cancer cells were the only potentially antigenic substances shared by the original vaccine and the skin test reagent. When the number of cultured cells was insufficient for skin testing, patients were either skin-tested with cells from the original tumor specimen, or the vaccination site was used as an immune response indicator. DTH reactions were measured at all skin test sites about 24 and 48 hours after injection. A positive response was defined as a wheal and flare reaction with a diameter greater than or equal to 4 mm. To determine whether GM-CSF itself stimulated local reactions, 100 micrograms of GM-CSF was injected intradermally on the right anterior forearm, and the sites were similarly assessed.

Step 2: Production and Proliferation of Effector T Lymphocytes

Two weeks after the second immunization, mononuclear white blood cells ("WBCs") were isolated from non-mobilized peripheral blood through a Quinton catheter in the subclavian vein using a cell separator. The total number of leukocytes obtained from individual leukaphereses varied between about $5 \times 10^9$ and $3 \times 10^{10}$. Patients were leukaphere-sed two or three times on successive days for each treatment. Differential counts were obtained on all samples. Lymphocytes contributed between 40–90% of total cells. RBCs were removed from all samples by selective lysis with tris-ammonium chloride prior to culture. WBCs were suspended in tissue culture medium supplemented with antibiotics and autologous serum (culture medium). Anti-CD3 ("OKT3™") was added to the cell mixture, and the cells were placed in tissue culture flasks. Cells were incubated at approximately 37° C. for about 48 hours. IL-2 (100 IU/ml) then was added to the anti-CD3 stimulated cells. Cells then were grown for three to five days and, after reaching maximum density, cells were harvested into IV infusion bags. Count and viability were determined. Morphologic analysis was performed by differential counting of cytocentrifuged, stained cells. The harvested cells were tested for endotoxin and microbial and fungal contamination.

Step 3: Infusion of Activated T Lymphocytes

Patients received COMPANZINE® (10 mg IV push), BENADRYLE® (25–50 mg IV push) and TYLENOL® (650 mg PO) prior to infusion of cells. Sterile, endotoxin free cells were infused into patients through a peripheral vein over a 1–3 hour period in an outpatient IV infusion facility. The numbers of cells infused are detailed in Table 3. If patients experienced chills, they received DEMEROL® (25 mg IV push) that was repeated as needed. Patients were monitored for toxicity for three hours following completion of cell infusion.

Patients also received IL-2 by bolus by IV infusion once daily. The patients received about $3 \times 10^6$ IU of IL-2 per day on alternate days for 10 days (5 treatments). This amount of IL-2, which is generally regarded as being low dose, has not been associated with any clinical effects when used by itself either in animal models or humans.

Results: Vaccination

As discussed above, the DTH response was directed exclusively against breast cancer cell associated antigens. The breast cancer patient DTH results are detailed in Table 2. With one exception, DTH reactions failed to develop at primary immunization sites, demonstrating that the vaccine did not non-specifically stimulate local inflammatory responses. Positive DTH responses were detected following primary vaccination in 14 of 15 patients. The physical characteristics and kinetics of the responses were typical of classical DTH reactions.

TABLE 2

Vaccination results

| Patient # | # cells | Adjuvant | 1° site DTH | 2° site DTH | Skin test | GM-CSF |
|---|---|---|---|---|---|---|
| HT-95-56 | $5 \times 10^6$ | GM-CSF | negative | positive | ND | negative |
| HT-95-62 | $1 \times 10^7$ | GM-CSF | negative | positive | ND | negative |
| HT-96-4 | $2 \times 10^7$ | GM-CSF | negative | negative | ND | negative |
| HT-96-32 | $1 \times 10^7$ | GM-CSF | negative | positive | ND | negative |
| HT-96-47 | $1 \times 10^7$ | GM-CSF | negative | positive | ND | negative |
| HT-97-3 | $2 \times 10^7$ | GM-CSF | >40 mm | positive | 35 mm | negative |
| HT-97-4 | $2 \times 10^7$ | GM-CSF | negative | positive | 30 mm | negative |
| HT-97-6 | $2 \times 10^7$ | GM-CSF | negative | positive | 12 mm | negative |
| HT-98-1 | $2 \times 10^7$ | GM-CSF | negative | negative | 50 mm | negative |
| HT-98-3 | $2 \times 10^7$ | GM-CSF | negative | positive | >30 mm | negative |
| HT-98-15 | $2 \times 10^7$ | GM-CSF | negative | negative | 20 mm | negative |
| HT-98-18 | $2 \times 10^7$ | GM-CSF | negative | positive | ND | negative |
| HT-98-73 | $1 \times 10^7$ | GM-CSF | negative | positive | 14 mm | negative |
| HT-99-2 | $2 \times 10^7$ | GM-CSF | negative | positive | 28 mm | negative |
| HT-99-35 | $1 \times 10^7$ | GM-CSF | negative | positive | 4 mm | negative |

[1]NA-not applicable; ND-not done

The results clearly demonstrated for the first time that breast cancer cells are immunogenic in the host of origin and that most if not all breast cancer patients have immunogenic cancers. This means that breast cancer is potentially susceptible to immunotherapy. The study also demonstrated that the presence of advanced breast malignancy does not prevent generation of autologous cancer antigen-specific immune responses. The patients were not tolerized to their own cancers. Systemic specific or non-specific immune suppression is unlikely to be the explanation for the failure of cancer patients to develop immunity against their own progressing malignancies. The results also demonstrated that various forms of standard and experimental chemotherapy, including dose intensive chemotherapy followed by stem cell reconstitution, that are routinely used to treat breast cancer, do not permanently prevent cancer antigen-specific immune responses from being generated in vivo.

Results: Growth Characteristics of OKT3™-Stimulated Cells

As discussed above, vaccination with autologous cancer cells primes T lymphocytes and induces immune responses that protect vaccinated animals from developing tumors. Adoptive transfer of cancer antigen-specific effector T lymphocytes produces rejection of progressing malignancies. Stimulating T lymphocytes from immunized animals with anti-CD3 converts lymphocyte populations that contain high numbers of primed cancer antigen specific T lymphocytes into lymphocyte populations that contain high numbers of cancer antigen-specific effector T lymphocytes. Anti-CD3 therefore is one of the most effective methods of T lymphocyte activation for tumor treatment and has the advantage of being readily applicable to development of similar strategies for humans. Despite the fact that anti-CD3 is a non-specific T lymphocyte stimulant, the in vivo anti-cancer effects of the effector T lymphocytes are cancer antigen specific. A second purpose of the current example therefore was to determine whether activated T lymphocytes could be routinely produced from the peripheral blood of immunized breast cancer patients using an anti-CD3/IL-2 stimulation strategy.

As seen in Table 3, all patients'cells exhibited vigorous growth in response to OKT3 ™ and IL-2. Several general observations can be made about the growth patterns that developed as the cultures progressed. Monocytes attached to the surface of culture flasks within the first hour. By twenty-four hours, lymphocytes had attached to the surface of some of the adherent cells, forming monocyte/lymphocyte clusters. Lymphocytes that were attached to adherent cells also underwent morphological changes, mainly evidenced by increase in size. In contrast, cultures that contained no OKT3 ™ (IL-2 control) exhibited no lymphocyte attachment to adherent cells or morphological alterations. Lymphocytes remained small and round and free in solution. Although the number of attached lymphocytes increased .-lo with time, and the proportion of the adherent cells with attached lymphocytes also increased with time, there was no evidence for cell proliferation during the OKT3 ™ phase. There was no increase in cell number when cell counts were performed on cultures to which no IL-2 was added (OKT3 ™ control).

TABLE 3

Growth of Patients' Mononuclear Cells Following Anti-CD3/IL-2 Stimulation

| Patient # | Starting # cells | Starting differential[1] | Final product # cells | % Lymphs Morph/CD3 | CD4/CD8 |
|---|---|---|---|---|---|
| HT-95-23 | $2.5 \times 10^{10}$ | 75/18/7 | $1.6 \times 10^{10}$ | 92/88 | .62 |
| HT-95-50 | $1.9 \times 10^{10}$ | 57/27/16 | $1.6 \times 10^{10}$ | 92/86 | 4.4 |
| HT-95-55 | $3.6 \times 10^{10}$ | 51/11/38 | $4.7 \times 10^{10}$ | 94/98 | 2.3 |
| HT-95-12 | $2.2 \times 10^{10}$ | 66/17/17 | $5.0 \times 10^{10}$ | 96/ND | ND[2] |
| HT-95-62 | $2.5 \times 10^{10}$ | 70/19/11 | $7.0 \times 10^{10}$ | 99/95 | 2.5 |
| HT-95-56 | $1.7 \times 10^{10}$ | 75/21/4 | $4.3 \times 10^{10}$ | 98/95 | 2.1 |
| HT-96-4 | ND | | | | |
| HT-96-32 | $3.0 \times 10^{10}$ | 73/17/10 | $5.6 \times 10^{10}$ | 99/ND | ND |
| HT-96-47 | $2.1 \times 10^{10}$ | 60/30/10 | $5.4 \times 10^{10}$ | 96/92 | 1.0 |
| HT-97-3 | $4.6 \times 10^{10}$ | 83/14/2 | $8.3 \times 10^{10}$ | 96/ND | ND |
| HT-97-4 | $3.3 \times 10^{10}$ | 69/28/3 | $9.3 \times 10^{10}$ | 97/ND | ND |
| HT-97-6 | $3.1 \times 10^{10}$ | 44/37/19 | $4.5 \times 10^{10}$ | 85/ND | ND |
| HT-98-1 | $2.7 \times 10^{10}$ | 83/13/1 | $8.3 \times 10^{10}$ | 90/10 | 1.5 |
| HT-98-3 | $3.0 \times 10^{10}$ | 89/8/3 | $3.8 \times 10^{10}$ | 93/ND | ND |
| | $4.4 \times 10^{10}$ | 84/15/1 | $1.4 \times 10^{11}$ | 91/96 | 3.9 |
| HT-98-15 | $2.5 \times 10^{10}$ | 70/15/10 | $5.4 \times 10^{10}$ | 97/90 | .4 |
| | $4.3 \times 10^{10}$ | 86/10/4 | $1.1 \times 10^{11}$ | 89/95 | 1.4 |
| HT-98-73 | $2.6 \times 10^{10}$ | 75/16/8 | $8 \times 10^{10}$ | 95/90 | 2.3 |
| HT-99-2 | $2.6 \times 10^{10}$ | 55/25/18 | $1.0 \times 10^{11}$ | 85/93 | 3.5 |
| HT-99-11 | $2.6 \times 10^{10}$ | 72/28/6 | $6.0 \times 10^{10}$ | 93/93 | 1.7 |
| HT-98-18 | $3.3 \times 10^{10}$ | 64/14/22 | $2.2 \times 10^{10}$ | 99/ND | ND |
| | $3.0 \times 10^{10}$ | 66/28/6 | $1.1 \times 10^{11}$ | 88/94 | .7 |

[1]Lymphocytes/monocytes/granulocytes obtained from unimmunized breast cancer patients
[2]ND-not done Several noteworthy changes occurred after the IL-2 was added. There was a dramatic increase in the size of lymphocytes in the adherent cell complexes. The numbers of cells in the complexes increased, and, as cell growth proceeded in the complexes, the complexes gradually detached from the surface of the flask. The culture then came to be comprised by floating cell complexes and free lymphocytes. Morphological examination of the cells in floating complexes revealed numerous mitotic cells. As lymphocytes proliferated, the complexes became progressively smaller until, with most patients, the final population that was administered was mono-disperse with very few lymphocyte complexes evident. Nearly all of the monocytes that were present in the original cultures came to be included in the complexes, but when cultures were terminated there were very few monocyte/macrophages left. As shown in Table 3, the harvested cultures almost invariably were comprised primarily of T lymphocytes. The number of B lymphocytes (CD20+cells) remaining in the cultures was negligible (data not shown). The number of cells expressing NK or activated NK markers was negligible.

Growth controls were performed to control for OKT3 ™ and IL-2 stimulated differentiation and proliferation. Mononuclear cells cultured in the absence of OKT3 ™ and up to 100 IU/ml of IL-2 remained viable, but exhibited no evidence for either differentiation or proliferation. Mononuclear cells cultured in the presence of OKT3 ™ but receiving no IL-2 at any time during the culture period exhibited the OKT3 ™ stimulated morphological changes, but failed to proliferate to any significant extent. Cells cultured for 48 hours in the absence of OKT3 ™ then stimulated with IL-2 exhibited no complex formation, morphological changes or evidence of proliferation.

T lymphocytes that were harvested at the end of the culture period invariably expressed high levels of T lymphocyte activation markers, including CD25, CD69 and HLADr as depicted in Table 4. Unstimulated circulating T lymphocytes do not normally express significant levels of those markers, but the starting populations were not completely negative, because CD69 and HLADr positive non-T lymphocytes also were present.

TABLE 4

Phenotypic Changes in Mononuclear Cells Induced by Anti-CD3/IL-2

| | Cell Phenotype | | | | | | |
|---|---|---|---|---|---|---|---|
| Source | CD3[1] | CD4 | CD8 | CD56 | CD25 | CD69 | HLADr |
| HT-98-3 | 63/96 | 35/74 | 18/19 | <¼ | 3/81 | 19/46 | 12/74 |
| HT-98-15 | 74/90 | 39/27 | 23/69 | <1/7 | <1/56 | 35/52 | 44/54 |
| HT-98-18 | 66/94 | 41/41 | 14/55 | <¼ | <1/82 | 12/50 | 19/70 |

[1]Data are expressed as percent positive cells before and after culture.

There were several reasons for choosing peripheral blood as the T lymphocyte source. First, it is easily accessible and renewable. Moreover, current understanding of how immune responses develop following vaccination is that local injection of antigen leads to production of primed antigen-specific T lymphocytes in LNs draining immunization sites. The primed T lymphocytes then are released from LNs into the circulation so that they may be carried to sites of antigen exposure. This must have occurred during the current study as evidenced by the fact that DTH reactions occurred at skin test sites. Some of the circulating primed cancer antigen-specific T lymphocytes left the peripheral blood, entered the skin and interacted with cancer antigen and antigen-presenting cells to produce a local immune response. Therefore, peripheral blood from vaccinated patients contains primed cancer antigen specific T lymphocytes that may be converted to effector cells by anti-CD3/ IL-2 stimulation. In theory, since all antigen primed T lymphocytes should be released from lymphoid tissue into the circulation, peripheral blood should be the best source for effector precursors.

In summary, this example demonstrated that the combination of OKT3 ™ and IL-2 produces selective expansion of the peripheral blood T lymphocyte compartment in breast cancer patients immunized with their own cancer cells. One can infer from similar animal studies that the number of cancer antigen-specific effector cells in final populations was directly proportional to the numbers of primed cancer antigen specific T lymphocytes that were present at the outset.

Results: Toxicity

Phase I clinical trials have the additional purpose of allowing one to determine relative toxicity. Vaccination using GM-CSF as the adjuvant produced only transient grade I/ll toxicity. Transient fever was the most common side effect. Transient wheal and flare reactions were observed at secondary vaccination sites. There was no local tissue damage. No local growth of irradiated cancer cells occurred. It can be concluded that tumor cells themselves produced no significant toxicity and that the effective dose of GM-CSF produced no significant toxicity. The numbers of cells detailed in Table 3 were infused with no significant associated toxicity. There was only transient grade I/II toxicity, with fever being the most common side effect. The infusion of IL-2 had similar effects. In summary, CAI was performed in this group of breast cancer patients with no significant toxicity.

Results: Efficacy

Two general points can be made about the clinical responses observed during the current study of CAI in breast cancer patients. First, CAI did produce objective responses in treated breast cancer patients. As an example, FIG. 1 demonstrates the disappearance of a metastatic lung nodule in a treated patient HT-98-3. HT-98-3 had progressive chest wall disease as well as parenchymal lung disease. The chest wall mass, which was located in an intercostal space, was excised by a cardiothoracic surgeon. The diagnosis of breast cancer was confirmed and the tissue was sent to the immunotherapy lab for vaccine preparation. The patient then underwent high dose therapy and stem cell rescue. At 6 and 12 weeks post transplant the patient still had evidence of a 1×1 cm tumor. The patient was treated with CAI at that time and the lesion disappeared. That treatment was more than 1.5 years ago, and the patient has experienced no disease recurrence.

In the second patient, HT-98-18, an initial CR was obtained after high dose chemotherapy and stem cell rescue for chemotherapy resistant metastatic breast cancer. The patient then presented at routine radiological follow up with a left axillary lymph gland as well as some mediastinal glands. The axillary gland was removed and the tissue confirmed to contain breast cancer and was then used for CAI. The lymphadenopathy showed involution. After several months, certain of the mediastinal glands again became prominent. A biopsy was performed to obtain further tissue for immunotherapy. However none of the glands were shown to contain malignant tissue. Consequently the patient continues at this time with a surgical CR.

A third patient, HT-99-2, who had multiple liver metastases, was treated recently. Complete regression of liver nodules was documented by a CT scan. At this time, it is too soon to know whether this CR will correlate with increased survival.

Figure 2:
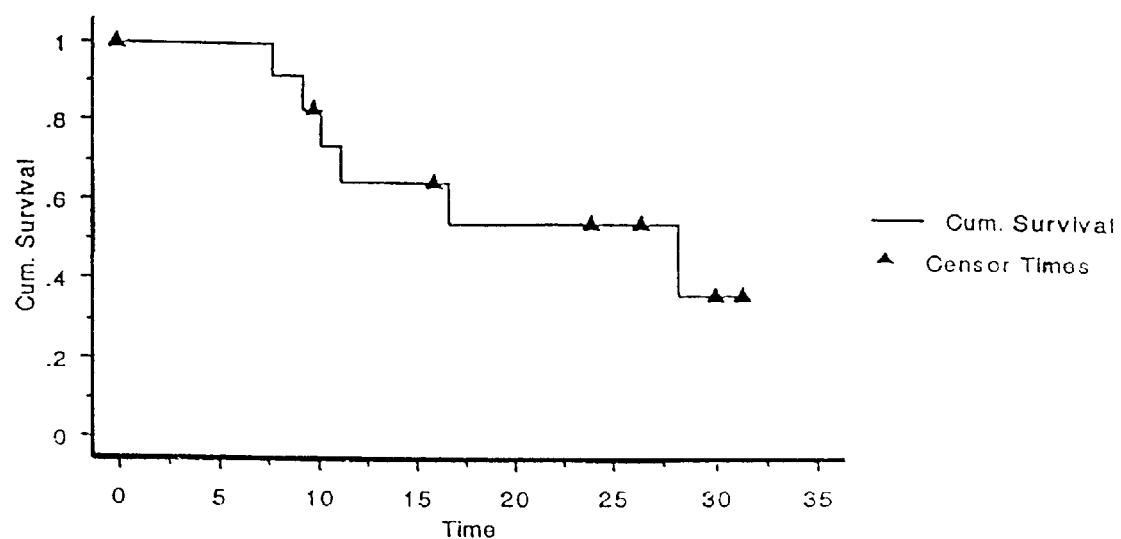
FIG. 2 shows a survival curve for patients receiving CAI after undergoing high-dose chemotherapy and stem cell rescue.

Second, it is important to stress in this regard that all of the breast cancer patients included in this example had advanced chemoresistant cancer, and most already had failed high dose chemotherapy and stem cell reconstitution. The two year survival rate for this group of patients is very low. Nevertheless, a high proportion of treated patients remain alive today. Most of these patients received no further treatment following immunotherapy. Current survival results are summarized in FIG. 2.

In summary, the results of phase I clinical trials have established breast cancer is immunogenic and that strong immune responses can be generated by immunizing patients with breast cancer cells and GM-CSF. High numbers of activated T lymphocytes can be produced from peripheral blood of patients with advanced breast cancer. Adoptive transfer of those activated T lymphocytes to patients can be safely achieved and will produce objective clinical responses. The risks of predicting therapeutic impact of a treatment modality from phase I data are well known.

C. ASTROCYTOMA EXAMPLE

Step 1: Vaccination

In this example, nine eligible patients all had operable, recurrent grade III or IV astrocytoma, had a Karnovsky score $\geq 60$ and had been tapered off steroids. All patients had previously failed total resection followed by conventional radiation (55–60 Gy) and chemotherapy. The recurrent tumors were resected and histopathologic diagnosis was confirmed on the recurrent tumor. All patients had radiological evidence of extensive progressing cancer and were being treated with steroids to control brain swelling at the time that their recurrent tumors were debulked for immunotherapy.

Cancer tissue was minced with scissors and suspended in medium containing an enzyme mixture manufactured by Life Technologies. Complete digestion was achieved within 1.5 to 2.0 hours at about 37° C. in a trypsinization flask. The cells were suspended in medium supplemented with 20% human AB+ serum and counted. Cells were irradiated at approximately 5000 rads and stored frozen at about −70° C. All cell preparations were greater than 80% viable and sterile.

At the time of vaccination, about $10^7$ cancer cells were mixed with a single vial of BCG containing approximately $10^8$ viable bacilli. The mixture was injected into four intradermal sites (0.25 ml/site), one each in the left and right axillae and left and right groin, chosen for maximal lymphoid drainage. All patients were immunized at least twice at two-week intervals.

Step 2: Production and Proliferation of Effector T Lymphocyes

Two weeks after the second immunization, mononuclear WBCs were isolated from peripheral blood by leukapheresis. Yields varied between $5\times10^9$ and $2\times10^{10}$ cells per leukapheresis. Patients were leukapheresed three times on successive days for each treatment. Lymphocytes contributed between 30–80% of total cells. WBCs were suspended in tissue culture medium supplemented with autologous serum. OKT3 ™ was added to the cell mixture, and the cells were placed in tissue culture flasks. Cells were incubated at about 37° C. for about 48 hours. Forty-eight hours later the cell mixture was suspended in culture medium containing IL-2. After reaching maximum density, cells were pooled and harvested into I infusion bags. Count and viability were determined. Morphologic analysis was performed by differential counting of cytocentrifuged, stained cells. Cells were immunophenotyped by fluorescent-activated cell sorter analysis with antibodies to CD3, CD4, CD8, CD25, CD71 and HLADr. The harvested cells also were tested for endotoxin and microbial and fungal contamination.

Step 3: Infusion of Activated T Lymphocytes

Sterile, endotoxin free lymphocytes were infused into all nine patients. Activated cells were infused into the blood stream over a six-hour period while patients were in the hospital. Patients remained in the intensive care unit of the hospital for observation for at least 48 hours after receiving cells. Patients were monitored neurologically and by complete laboratory work-up every four hours during the first forty-eight hours. Patients were monitored for toxicity using NCI Common Toxicity Criteria.

Results: Astrocytoma

No patient experienced more than 1+ toxicity, which is mild, transient toxicity. Most patients experienced transient fever, chills, and/or nausea during and immediately following intravenous administration of cultured cells. Response rate, disease free survival and overall survival were used to measure response to treatment. Tumor growth was monitored using magnetic resonance imaging MI) scans. Patients received MRI scans prior to treatment, one month after treatment, and every three months thereafter.

Figure 3:
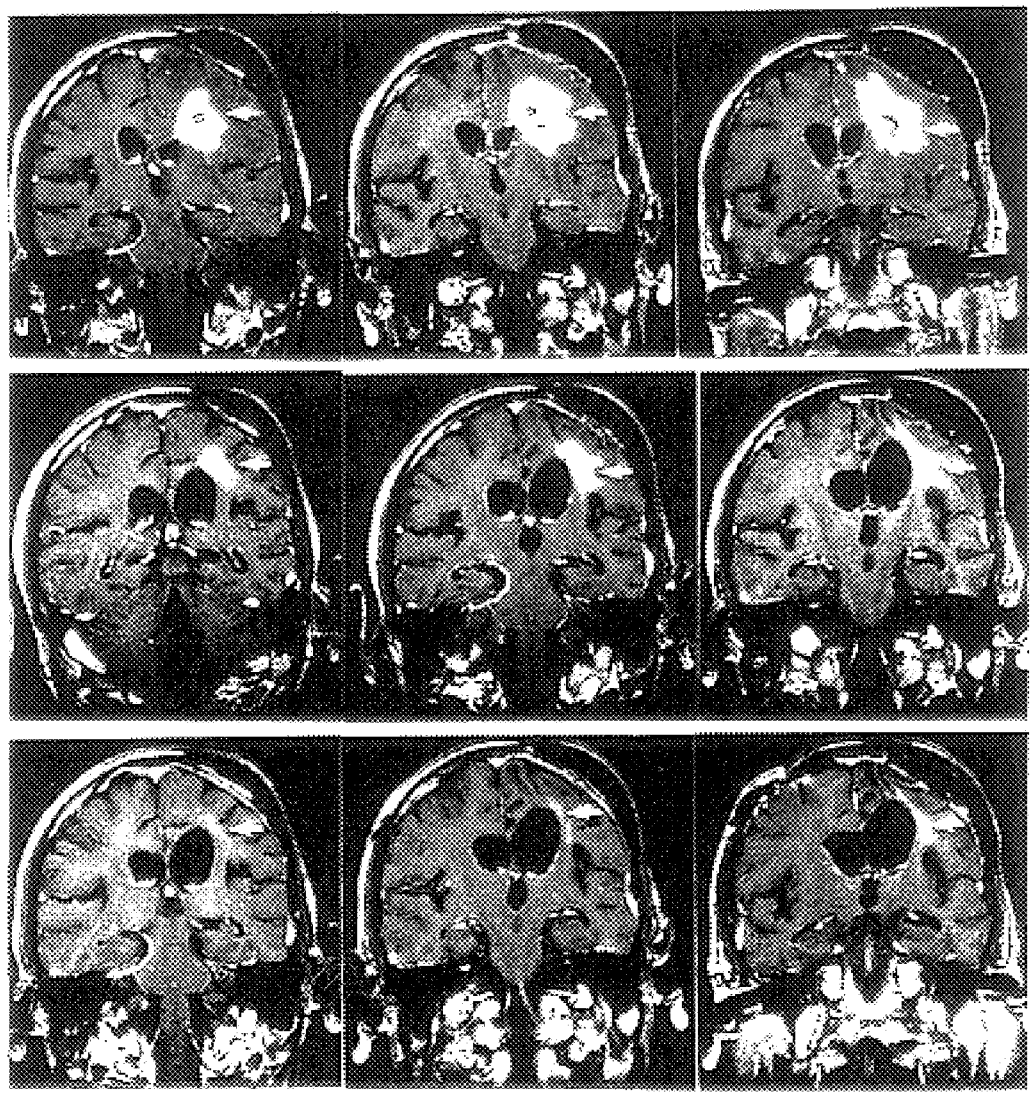
FIG. 3 shows serial MRI scans of an astrocytoma patient treated with CAI. The scans show the patient's astrocytoma on Feb. 16, 1995, three months after surgery and immediately prior to immunotherapy (top row), on May 15, 1995, two months after immunotherapy (center row), and on Nov. 20, 1995, eight months after immunotherapy (bottom row).
Figure 4:
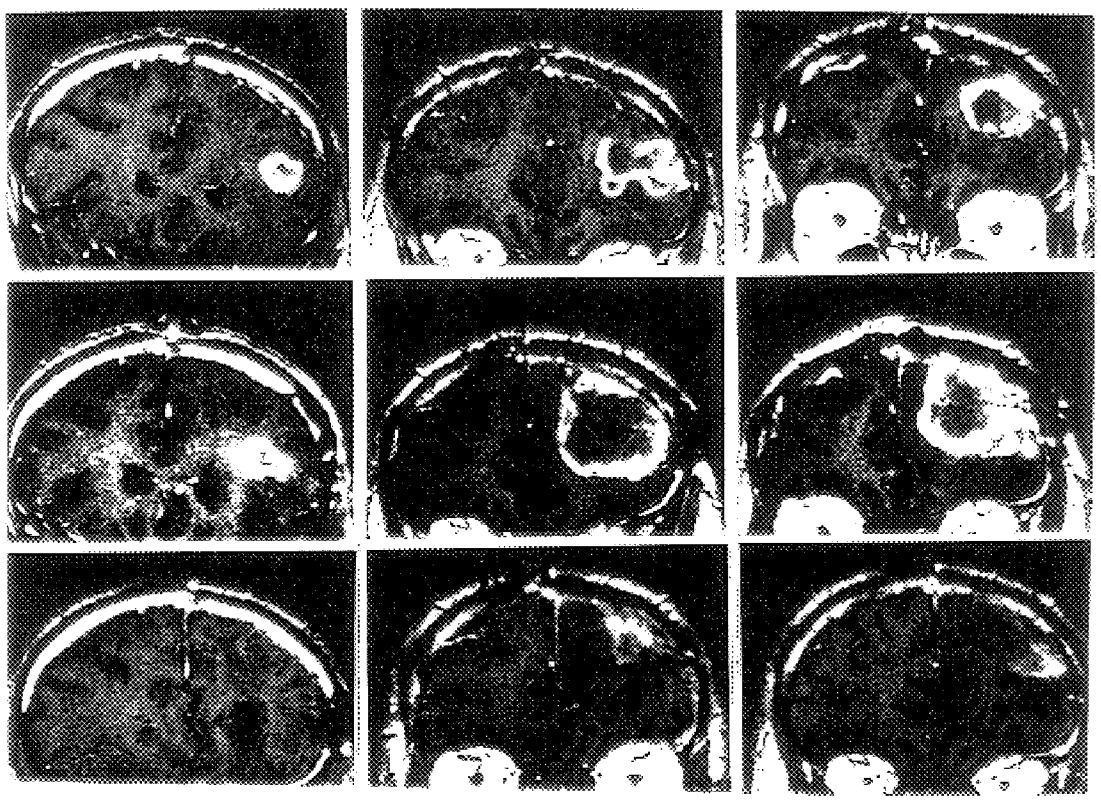
FIG. 4 shows a serial MRI scans of another astrocytoma patient treated with CAI. The scans show the patient's astrocytoma on Jan. 4, 1996, immediately prior to surgery (top row), on Mar. 27, 1996, three months after surgery and immediately after completion of immunotherapy, and on Oct. 20, 1997, eighteen months after immunotherapy.

Clinical responses are detailed in FIG. 3, FIG. 4 and Table 5. Patient#1 was treated three months after surgery for recurrent tumor at a time when progressive tumor growth was documented both clinically and on MRIs. As seen in FIG. 3, Patient#1's cancer progressively decreased in size following two courses of immunotherapy to the point where little or no cancer was detectable in the most recent MRI's. The patient is currently alive and well, although hemiparesis and speech difficulties, which were present prior to immunotherapy, remain unchanged. Patient#3's cancer exhibited a transient partial decrease in size following a single treatment, then continued to grow. There was no effect on survival. As shown in FIG. 4, Patient #5's cancer progressively decreased in size following two courses of immunotherapy to the point where little cancer was detectable in the most recent MRI's. The patient is alive and well with no noteworthy symptoms. He has returned to full-time employment. None of the patients received any potentially cytoreductive treatment other than immunotherapy. At the time that treatment failure was documented by post-immunotherapy tumor progression, patients received steroids to control brain swelling until they died.

TABLE 5

Effect of Immunotherapy On Patient Survival

| Patient (sex) | Age | Astrocytoma grade | Time to recurrence[1] | Lymphocytes infused | Route of infusion[2] | Survival post-recurrence[3] |
|---|---|---|---|---|---|---|
| 1 (M) | 41 | Grade III | 7 months | 1 $2.0 \times 10^{10}$ | IV | >4.5 years |
|  |  |  |  | 2 $1.0 \times 10^{10}$ | IV |  |
| 2 (M) | 62 | Grade IV | 6 months | 1 $1.3 \times 10^{10}$ | IV | 4 months |
| 3 (F) | 27 | Grade IV | 10 months | 1 $2.0 \times 10^{10}$ | IA | 5 months |
| 4 (M) | 52 | Grade IV | 13 months | 1 $1.0 \times 10^{10}$ | IV | 7 months |
| 5 (M) | 36 | Grade III | 6 months | 1 $7.8 \times 10^{10}$ | IA/IV | >3.5 years |
|  |  |  |  | 2 $7.3 \times 10^{10}$ | IA/IV |  |
| 6 (M) | 59 | Grade IV | 6 months | 1 $4.6 \times 10^{10}$ | IV | 6 months |
| 7 (M) | 66 | Grade IV | 4 months | 1 $6.3 \times 10^{10}$ | IA/IV | 6 months |
|  |  |  |  | 2 $7.4 \times 10^{10}$ | IA/IV |  |
| 8 (M) | 31 | Grade III | 8 months | 1 $7.1 \times 10^{10}$ | IA | 13 months |
|  |  |  |  | 2 $9.6 \times 10^{10}$ | IA/IV |  |
| 9 (F) | 65 | Grade IV | 12 months | 1 $7.0 \times 10^{10}$ | IA | 10 months |
|  |  |  |  | 2 $2.0 \times 10^{10}$ | IA |  |

[1] Interval between initial debulking surgery and debulking surgery for immunotherapy.
[2] Activated T Lymphocytes were infused either intravenously (IV) through an arm vein or intraarterially (IA) through the carotid artery. Some patients received cells both intraarterially and intravenously.
[3] Time from surgical debulking of recurrent tumor to death.

These results show that CAI is clinically effective against brain cancer. Adoptively transferred lymphocytes produced objective regressions in three of nine treated patients, and regression was correlated with improved clinical status in two of those patients. At the time that surgical resection and immunotherapy were initiated, all of the patients in this study had rapidly progressing grade III/V astrocytomas that required steroids to control brain swelling. Historically, these cancers invariably progress, and patients die within a few months. Surgical resection alone does not dramatically prolong patient survival. Neither of the responding patients required or received additional treatment. The fact that two of the patients are still alive with no tumor regrowth more than three years later is a novel finding that can only be attributed to CAI.

D. RENAL CELL CARCINOMA EXAMPLE

A key difference between the application of CAI to experimental and human cancers has been timing, and the difference in outcome could be directly related to those differences. In animal models, the treated individuals had small homogeneous cancers that were created a few days earlier by injecting cancer cells. In contrast, with only rare exceptions, the cancer patients that were treated with CAI in Phase I studies all had widespread stage IV cancer that had resisted various non-immunologic treatment strategies. CAI had no apparent effect on disease progression when it was used to treat experimental animals that had extensive disease. Therefore, a single case will be described to illustrate possible CAI outcome if CAI is administered early in disease progression at a time when patients only have micro-metastatic disease.

A 34-year-old male was diagnosed with kidney cancer. An exploratory laparotomy was performed, and the patient's left kidney was found to contain a large mass that later proved to be a renal cell carcinoma. The kidney was removed and the cancer was subjected to pathological analysis. The cancer weighed about 2.2 kilograms (5 lbs.), had invaded blood vessels and was diagnosed as stage IIIb renal cell carcinoma. Surgical removal of the cancer is the sole effective treatment for renal cell carcinoma. Renal cell carcinomas are widely regarded as being resistant to all forms of chemotherapy. The prognosis for patients with stage III renal cell cancer is very poor. The patient volunteered for my clinical trial. The patient was vaccinated twice with his own cancer cells and developed a positive DTH reaction. He then was treated with a single course of CAI in which he received about $4.8 \times 10^{10}$ anti-CD3 activated autologous T lymphocytes followed by a 5-day course of IL-2 at about $3 \times 10^6$ IU/day. The patient is alive and disease-free now more than four years later. The probability of surgical cure is relatively low in patients with this advanced disease.

Two additional renal cell cancer patients have been successfully treated with CAI during the past two years. Both patients had stage IV disease at the time of treatment, were treated twice, and remain disease free more than 1.5 years later. Although the sample size is small, the data suggests that CAI can be effective against stage ImI and IV renal cell cancers and may actually be capable of permanently eliminating cancer cells from the patients' bodies.

E. SUMMARY

The breast cancer study demonstrated that most if not all breast cancers are immunogenic and that strong immune responses can be generated by immunizing patients with breast cancer cells and GM-CSF. The question immediately arises as to whether these vaccination results are generalizable to other types of malignancies. In other words, does the fact that breast cancers are immunogenic mean that brain cancers, colon cancers, ovarian cancers, leukemias, lung cancers, lymphomas, kidney cancers, prostate cancers and other common types of cancer are similarly immunogenic. The theoretical answer is that all cancers go through the same general types of genetic changes leading to malignant transformation and are susceptible to additional genetic changes during subsequent malignant proliferation. It is those genetic changes that are responsible for the immunogenicity of malignant cells. Therefore, other malignancies should be similarly immunogenic. The experimental answer is that, studies using autologous cancer cells and BCG as vaccines have established that some brain cancers, colon cancers, ovarian cancers, melanomas and renal cell cancers are immunogenic. During the course of my studies employing vaccination with autologous cancer cells and GM-CSF, over 50 patients have been vaccinated with a wide variety of other advanced malignancies, including, astrocytoma (23), neuroblastoma (2), medulloblastoma (1), ovarian carcinoma (3), renal cell carcinoma (8), melanoma (16), colon carcinoma (6) and lung carcinoma (3). The responses that have been obtained in those patients, all of which had advanced malignancy, were qualitatively and quantitatively similar to the responses detailed above for breast cancer patients. That is, the patients had immunogenic neoplasms.

It is understood that the examples and embodiments described herein are for illustrative purposes only and that various modifications or changes in light thereof will be suggested to persons skilled in the art and are to be included within the spirit and purview of this application and scope of the appended claims.

I claim:

1. A cancer immunotherapy method for treating cancer in a patient comprising:

vaccinating a patient with a vaccine comprised of the patient's own malignancy and an immunologic adjuvant;

removing primed T lymphocytes from the peripheral blood of the patient;

stimulating the primed T lymphocytes to differentiate into effector lymphocytes in vitro;

stimulating the effector T lymphocytes to proliferate in vitro; and infusing the effector T lymphocytes back into the patient.

2. The cancer imuntheapy method in claim 1 wherein the immunologic adjuvant is GM-CSF.

3. The cancer immunotherapy method in claim 1 wherein the removal step in performed by leukapheresis.

4. The cancer immunotherapy method in claim 1 wherein the differentiation step is performed using anti-CD3.

5. The cancer immunotherapy method in claim 1 wherein the proliferating step is performed using IL-2.

6. The cancer immunotherapy method in claim 1 wherein the cancer immunotherapy is directed to the treatment of breast cancer.

7. The cancer immunotherapy method in claim 1 wherein the cancer immunotherapy is directed to the treatment of astrocytoma.

8. The cancer immunotherapy method in claim 1 wherein the cancer immunotherapy is directed to the treatment of renal cancer.

9. The cancer immunotherapy method in claim 1 wherein the patient is vaccinated at multiple body sites.

10. The cancer immunotherapy method in claim 1 wherein the patient is treated at the time of initial diagnosis.

11. The cancer immunotherapy method in claim 1 wherein the patient is treated immediately following surgical removal of cancer.

12. The cancer immunotherapy method in claim 1 wherein the patient is treated with sudpopulations of activated peripheral blood T lymphocytes.

* * * * *